United States Patent [19]
De Nardo et al.

[11] Patent Number: 5,478,962
[45] Date of Patent: Dec. 26, 1995

[54] PROCESS FOR THE SYNTHESIS OF DIMETHYLCARBONATE

[75] Inventors: Laura De Nardo, Monza; Maurizio Ghirardini, Milan; Gianni Donati, Rho, all of Italy

[73] Assignee: Enichem S.p.A., Milan, Italy

[21] Appl. No.: 391,169

[22] Filed: Feb. 21, 1995

[30] Foreign Application Priority Data

Mar. 25, 1994 [IT] Italy ................... MI94A0571

[51] Int. Cl.$^6$ ................... C07C 68/00
[52] U.S. Cl. ................... 558/277; 48/198.1; 48/198.3; 568/910
[58] Field of Search ............ 558/277; 568/910

[56] References Cited

U.S. PATENT DOCUMENTS

| | | | |
|---|---|---|---|
| 5,142,087 | 8/1992 | Joerg et al. | 558/277 |
| 5,159,099 | 10/1992 | Romano et al. | 558/277 |
| 5,206,409 | 4/1993 | Romano et al. | 558/277 |
| 5,210,269 | 5/1993 | Di Muzio et al. | 558/277 |

FOREIGN PATENT DOCUMENTS

| | | |
|---|---|---|
| 9300312 | 3/1993 | Belgium . |
| 1006181 | 5/1994 | Belgium . |
| 0134668 | 3/1985 | European Pat. Off. . |
| 0460735 | 12/1991 | European Pat. Off. . |

*Primary Examiner*—Johann Richter
*Assistant Examiner*—Michael G. Ambrose
*Attorney, Agent, or Firm*—Stevens, Davis, Miller & Mosher

[57] ABSTRACT

Process for the preparation of dimethylcarbonate which consists in feeding oxygen and a mixture of methanol and carbon monoxide to the reactor, with a molar ratio methanol/carbon monoxide of between 1 and 2, this mixture coming directly from the non catalytic direct oxidation of methane with oxygen characterized in that the above molar ratio between methanol and carbon monoxide, with fixed temperature and pressure values, is obtained by maintaining the ratio between methane and oxygen between 1 and 100, by injections of fresh oxygen into a tubular reactor, during the above oxidation reaction.

5 Claims, 1 Drawing Sheet

PROCESS FOR THE SYNTHESIS OF DIMETHYLCARBONATE

The present invention relates to a process for the synthesis of dimethylcarbonate.

More specifically the present invention relates to a process for the synthesis of dimethylcarbonate starting from oxygen and a mixture of methanol and carbon monoxide obtained by the non catalytic direct oxidation of methane with oxygen.

Dimethylcarbonate (DMC hereafter) is an extremely versatile chemical product which is used as organic solvent and additive for fuels, or as a reagent, as a substitute of phosgene, in the synthesis of other alkyl or aryl carbonates used as synthetic lubricants, solvents, plasticizers and monomers for organic glass and in methylation and carbonylation reactions for the preparation of isocyanates, urethanes and polycarbonates. DMC is in fact becoming the most important intermediate in the synthesis of polycarbonate and, as is known, is a polymeric material with a wide range of uses owing to its excellent characteristics of transparency, shock-resistance and processability.

The synthesis of DMC starting from methanol, carbon monoxide and oxygen, in the presence of a catalyst, is described in numerous patents such as, for example, U.S. Pat. Nos. 3,114,762, 3,227,740, 3,846,468, 3,952,045, 4,360,477, which differ in the type of catalyst used.

A particularly convenient synthesis method is based on reaction (I) below:

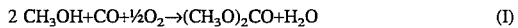

$$2\ CH_3OH + CO + \tfrac{1}{2}O_2 \rightarrow (CH_3O)_2CO + H_2O \qquad (I)$$

in which a copper salt, particularly CuCl, is used as catalyst, according to the procedure described in European patent applications publication EP 460.732 and EP 460.735.

The methanol used in the processes for the production of DMC is normally obtained from the synthesis gases coming from the reforming of gaseous saturated hydrocarbons such as natural gas, methane or light liquids. The best mixture of synthesis gases for methanol is generally that wherein the ratio $(H_2-CO)/(CO+CO_2)$ is slightly higher than 2 and can be conveniently obtained by primary reforming (steam reforming) followed by secondary reforming which consists of a combustion with oxygen of the gases coming from the primary reforming (autothermal reforming).

An alternative solution to the process through steam reforming consists of the direct oxidation of methane with oxygen to methanol, in the presence of a catalyst. This solution, however, has a disadvantage due to the considerable production of carbon dioxide which thus cuts down the reagent to the main reaction.

One way of overcoming this drawback consists in producing methanol by the direct oxidation of methane non catalytically. This process, which can be schematized as follows (II):

$$(a)CH_4 + (b)O_2 \rightarrow (c)CH_3OH + (d)CO + (e)CO_2 + (f)CH_2O + (g)H_2O \qquad (II)$$

is not considered convenient, in terms of industrial feasibility, for producing methanol as it shows a selectivities not higher than 60%–65%. In this case however the loss of methane consists of carbon monoxide (20%–35%) whereas, the production of carbon dioxide is kept within acceptable limits (5%–15%). It should also be noted that there is the formation of small quantities of formaldehyde (1%–5%) as shown in reaction (II).

The non catalytic direct oxidation reaction of methane with oxygen can be carried out, for example, using a molar ratio between methane and oxygen of between 7 and 20, at a temperature of between 400° C. and 500° C. and at a pressure of between 10 and 70 atm.

In fact, operating under the above conditions, it is possible to obtain methanol and carbon monoxide in a molar ratio of between 1 and 2 (see Table 1).

TABLE 1

| $CH_4/O_2$ | Temper. (°C.) | Pressure (Atm.) | $CH_3OH/CO$ | Conversion $CH_4$ |
|---|---|---|---|---|
| 10 | 450 | 10 | 1 | 10 |
| 12 | 450 | 40 | 1.5 | 8 |
| 16 | 450 | 40 | 2.1 | 4.23 |
| 18 | 450 | 70 | 2 | 6 |

Table 1 above clearly shows that, by regulating the molar ratio between methane and oxygen, the ratio between methanol and carbon monoxide can be regulated in the mixture obtained from the direct non catalytic oxidation of methane.

During the above oxidation reaction the oxygen is fed in a pure form or mixed with other gases or air to a tubular reactor. It is known that oxygen introduced into the feeding is completely consumed in about 2 seconds in a chain of reactions of radical type and that the conversion of the methane depends on the molar ratio between methane and oxygen and, using the ratios between methane and oxygen and the temperature and pressure values indicated in Table 1, is between 4% and 10%.

During the synthesis process of DMC, as described, for example, in the above patents, the methanol is fed to the reactor together with a flow of carbon monoxide and oxygen in order to maintain, depending on the selectivity of the reaction, a molar ratio between methanol and carbon monoxide of between 1 and 2.

The Applicant has now found an improved process for the synthesis of DMC by feeding to the reactor oxygen and a mixture of methanol and carbon monoxide, coming from the direct non catalytic oxidation of methane with oxygen, wherein the molar ratio between the methanol and carbon monoxide can be maintained within a certain range of values by regulating the feeding of oxygen during the above oxidation reaction. In fact it has been found a way of increasing the conversion of the methane with respect to the known art described above, with obvious advantages relating to the plant engineering, maintaining the molar ratio between methanol and carbon monoxide within the limits suitable for the synthesis of DMC, which consists of a system wherein a series of injections of fresh oxygen are effected in different points of a tubular reactor, before the termination reactions completely extinguish the radicalic chains created during the previous injection.

The present invention therefore relates to a process for the preparation of dimethylcarbonate which consists in feeding to the reactor oxygen and a mixture of methanol and carbon monoxide, with a molar ratio methanol/carbon monoxide of between 1 and 2, this mixture coming directly from the direct non catalytic oxidation of methane with oxygen characterized in that, the above molar ratio between methanol and carbon monoxide, once the temperature and pressure values have been fixed, is obtained by maintaining the ratio between methane and oxygen between 1 and 100, by means of injections of fresh oxygen to a tubular reactor, during the above oxidation reaction.

Figure 1:
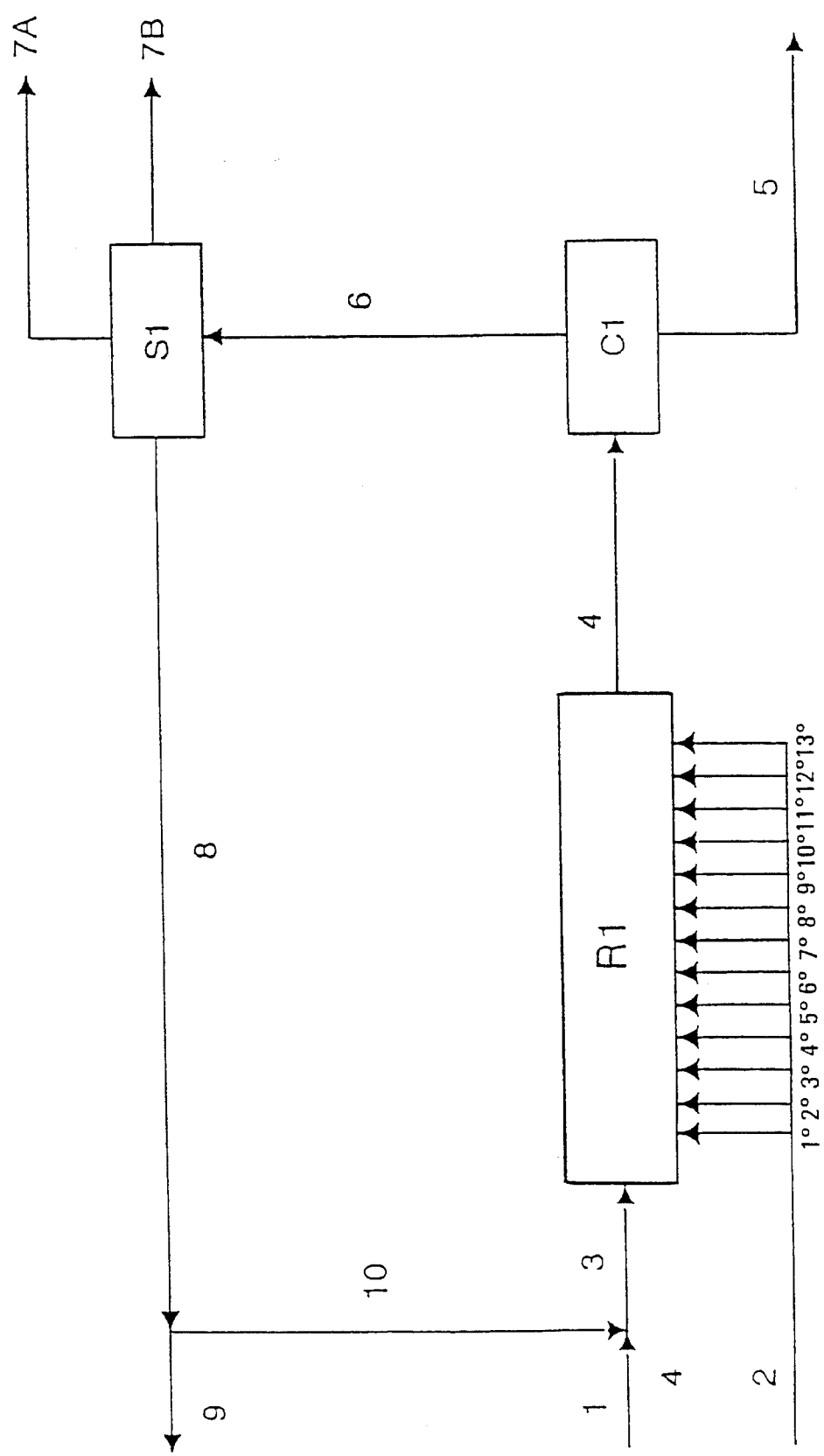
FIG. 1 is a schematic diagram of process equipment and a reaction sequence of the invention.

For the purposes of the present invention, at least two injections of fresh oxygen are necessary. These injections are carried out in order to maintain the molar ratio between methanol and carbon monoxide constant, thus obtaining a mixture which can be used in the synthesis of DMC.

Operating at a temperature and pressure and with molar ratios between methane and oxygen which are different from those shown in Table 1, and with a suitable selection of the number of injections, quantity of oxygen introduced during the injection and residence time of the oxygen in the single step, the molar ratio between methanol and carbon monoxide leaving the reactor can always be maintained within a range of between 1 and 2, with conversions of methane of up to 20%.

According to the present invention the oxidation reaction of methane with oxygen is carried out at a temperature of between 100° C. and 1000° C., preferably between 400° C. and 500° C., at a pressure of between 1 atm and 200 atm, preferably between 10 atm and 70 atm. The number of injections of fresh oxygen is at least two, the quantity of oxygen introduced in the single step is between 1% and 99%, preferably between 10% and 80%, the residence time of the oxygen in the single step is between $10^{-3}$ seconds and 1 minute, preferably between $10^{-2}$ and 3 seconds, the conversion of the methane is between 1% and 100%, preferably between 2% and 20% and the molar ratio between methane and oxygen is between 1 and 100, preferably between 5 and 30.

According to a preferred embodiment of the present invention, the molar ratio between methane and oxygen is equal to 16, the pressure is equal to 40 atm, the temperature is 450° C., the number of injections of oxygen into the reactor is equal to 2, the quantity of oxygen introduced in each single step is equal to 67% in the first step and 33% in the second step, the residence time of the oxygen in each single step is equal to 4.8 seconds in the first step and 2.7 seconds in the second step, the conversion of methane is equal to 6.3% and, in the mixture thus obtained, the molar ratio between methanol and carbon monoxide is equal to 2. This mixture will be used for the synthesis of DMC according to the known techniques in the art, as described for example in Italian patent application 20531 A/90.

Among the advantages deriving from the possibility of using the mixture of methanol and carbon monoxide obtained as described above directly for the production of DMC, there is the reduction of the upper section of the plant with respect to the conventional method which uses carbon monoxide and methanol coming from steam reforming. In addition, operating in this way, there is a decrease in investment costs with a consequent reduction in the production cost of dimethylcarbonate.

For a better understanding and embodiment of the present invention, an illustrative example is provided which does not however restrict the scope of the invention itself.

EXAMPLE 1

In the description of example 1 reference is made to the drawing of FIG. 1 wherein the numbers indicate flows of gas or liquid.

Table 2 shows the process quantification in tons/year (t/a).

Methane (1) and oxygen (2) are fed to the tubular reactor (R1), which is a reactor consisting of one or more steel pipes situated in parallel to each other, wherein:

both the conditions of instantaneous mixing of the gaseous reagents, and the absence of dead zones and back mixing of gas, are guaranteed by the suitable filling of inert material;

any possible catalytic effect of the metallic surfaces, which leads to the combustion of the methane, can be minimized by means of the suitable lining with inert material of the surfaces themselves;

the thermal exchange is outside the pipe in which the oxidation reaction takes place and can be obtained with a thermostating fluid such as, for example, water or the flow of gas itself being fed which is thus pre-heated;

The fresh oxygen is fed to the tubular reactor (R1) by means of injections in various points in order to maintain the ratio between methane and oxygen at the inlet at 5.3, and the ratio between methanol and carbon monoxide at the outlet at 1.3. The reactor is pressurized at 40 atm and heated to a temperature of 450° C.; the residence time of the oxygen in the single step is between 0.6 and 5 seconds, the number of injections is equal to 13 and the conversion of methane is equal to 18%. The quantity of oxygen introduced in each single step and the residence time are shown in Table 3.

The hot oxidation reaction products (4) are sent from the tubular reactor to a condenser (C1) where the two condensable and uncondensable phases are separated.

The condensable phase (5), mainly consisting of methanol, water and formaldehyde, is sent for the separation of the three components (said separation is not shown in FIG. 1).

The uncondensable phase (6), mainly consisting of non-reacted methane, carbon monoxide, carbon dioxide and possible inert products, passes to the separator (S1) where the carbon dioxide (7A) is separated by washing with methanol, and the carbon monoxide (7B) by washing with cuproammoniacal solutions (said separations are not shown in FIG. 1).

The non-reacted methane (8), after the discharge of any possible inert materials (9), is recycled (10) and, after adding fresh methane (1), is sent (3) to the tubular reactor (R1).

The methanol and carbon monoxide, recovered with means not shown in the FIGURE, are in such a molar ratio as to be able to be used for the synthesis of DMC which, in this case, is produced using a continuous process following the procedure described in Italian patent application 20530 A/90.

TABLE 2

| | PROCESS QUANTIFICATION AS TONS/YEAR | | | | | | | | | | |
|---|---|---|---|---|---|---|---|---|---|---|---|
| FLOWS | 1 | 2 | 3 | 4 | 5 | 6 | 7a | 7b | 8 | 9 | 10 |
| CH4 | 402,787 | 0 | 2,057,407 | 1,687,074 | 0 | 1,687,074 | 0 | 0 | 1,687,074 | 32,453 | 1,654,621 |
| O2 | 0 | 773,997 | 773,997 | 0 | 0 | 0 | 0 | 0 | 0 | 0 | 0 |
| N2 | 7,120 | 0 | 370,127 | 370,127 | 0 | 370,127 | 0 | 0 | 370,127 | 7,120 | 363,007 |
| CH3OH | 0 | 0 | 0 | 355,520 | 355,520 | 0 | 0 | 0 | 0 | 0 | 0 |
| CO | 0 | 0 | 0 | 239,791 | 0 | 239,791 | 239,791 | 0 | 0 | 0 | 0 |

TABLE 2-continued

| | PROCESS QUANTIFICATION AS TONS/YEAR | | | | | | | | | | |
|FLOWS|1|2|3|4|5|6|7a|7b|8|9|10|
|---|---|---|---|---|---|---|---|---|---|---|---|
|CO2|0|0|0|101,842|0|101,842|0|101,842|0|0|0|
|CH2O|0|0|0|34,719|34,719|0|0|0|0|0|0|
|H2O|0|0|0|412,4591|412,459|0|0|0|0|0|0|
|TOTAL|409,907|773,997|3,201,531|3,201,531|802,698|2,398,834|239,791|101,842|2,057,201|39,573|2,017,628|

TABLE 3

| STEP | OXYGEN INTRODUCED (%) | RESIDENCE TIME (seconds) |
|---|---|---|
| 1° | 22.81 | 4.76 |
| 2° | 11.23 | 2.73 |
| 3° | 8.95 | 1.97 |
| 4° | 7.71 | 1.56 |
| 5° | 6.96 | 1.31 |
| 6° | 6.42 | 1.13 |
| 7° | 5.93 | 0.99 |
| 8° | 5.61 | 0.89 |
| 9° | 5.29 | 0.81 |
| 10° | 5.07 | 0.75 |
| 11° | 4.85 | 0.69 |
| 12° | 4.69 | 0.65 |
| 13° | 4.48 | 0.61 |

We claim:

1. Process for the preparation of dimethylcarbonate which consists in feeding to the reactor oxygen and a mixture of methanol and carbon monoxide, with a molar ratio methanol/carbon monoxide of between 1 and 2, this mixture coming directly from the direct non catalytic oxidation of methane with oxygen characterized in that, the above molar ratio between methanol and carbon monoxide, once the temperature and pressure values have been fixed, is obtained by maintaining the ratio between methane and oxygen between 1 and 100, by means of injections of fresh oxygen to a tubular reactor, during the above oxidation reaction.

2. Process according to claim 1, wherein the oxidation reaction of methane with oxygen is carried out at a temperature of between 100° C. and 1000° C., a pressure of between 1 atm and 200 atms, the number of injections of fresh oxygen is at least 2, the quantity of oxygen introduced in each single step is between 1% and 99%, the residence time of the oxygen in each single step is between $10^{-3}$ seconds and 1 minute, the conversion of the methane is between 1% and 100% and the molar ratio between methane and oxygen is between 1 and 100.

3. Process according to claim 2, wherein the oxidation reaction of methane with oxygen is carried out at a temperature of between 400° C. and 500° C., a pressure of between 10 atm and 70 atms, the number of injections of fresh oxygen is at least 2, the quantity of oxygen introduced in each single step is between 10% and 80%, the residence time of the oxygen in each single step is between $10^{-2}$ and 3 seconds, the conversion of the methane is between 2% and 20% and the molar ratio between methane and oxygen is between 5 and 30.

4. Process according to claim 3, wherein the molar ratio between methane and oxygen is equal to 16, the pressure is equal to 40 atms, the temperature is 450° C., the number of injections of oxygen into the reactor is equal to 2, the quantity of oxygen introduced in each single step is equal to 67% in the first step and 33% in the second step, the residence time of the oxygen in each single step is equal to 4.8 seconds in the first step and 2.7 seconds in the second step, the conversion of the methane is equal to 6.3% and, in the mixture thus obtained, the molar ratio between methanol and carbon monoxide is equal to 2.

5. Process for the synthesis of dimethylcarbonate wherein the mixture of methanol and carbon monoxide obtained according to the process of claim 1, is used.

* * * * *